United States Patent [19]

Yagi

[11] Patent Number: 4,509,219
[45] Date of Patent: Apr. 9, 1985

[54] SLEEPING MATTRESS

[75] Inventor: Toshizo Yagi, Kodairashi, Japan
[73] Assignee: Japan Life Company Limited, Tokyo, Japan
[21] Appl. No.: 540,908
[22] Filed: Oct. 12, 1983
[51] Int. Cl.³ .............................................. A47C 27/22
[52] U.S. Cl. .......................................... 5/481; 5/448
[58] Field of Search ................... 5/481, 448, 468, 462, 5/464

[56] References Cited

U.S. PATENT DOCUMENTS

| 641,854 | 1/1900 | Gill | 5/448 |
|---|---|---|---|
| 2,831,532 | 4/1958 | Kasper | 5/481 |
| 3,016,317 | 1/1962 | Brunner | 5/420 |
| 3,974,532 | 8/1976 | Ecchuya | 5/481 |
| 4,143,435 | 3/1979 | Masuda | 5/481 |
| 4,330,892 | 5/1982 | Fukushima | 5/462 |

FOREIGN PATENT DOCUMENTS

| 552612 | 12/1959 | Belgium | 5/448 |
|---|---|---|---|
| 2698 | of 1888 | United Kingdom | 5/448 |
| 904253 | 8/1962 | United Kingdom | 5/481 |
| 2025234 | 1/1980 | United Kingdom | 5/448 |
| 2084010 | 4/1982 | United Kingdom | 5/448 |

Primary Examiner—Alexander Grosz
Attorney, Agent, or Firm—Browdy and Neimark

[57] ABSTRACT

A sleeping mattress comprises in order a first layer made of cushion material formed with wave-like projections, a second layer having semi-circular projections provided with permanent magnets, a third layer stuffed with palm fibers and reinforcing materials, and a fourth layer composed of cushion materials. A magnetic curing effect by the magnets and a spine balancing effect by moderate hardness are obtained during sleeping, and comfortable sleeping may be achieved.

7 Claims, 6 Drawing Figures

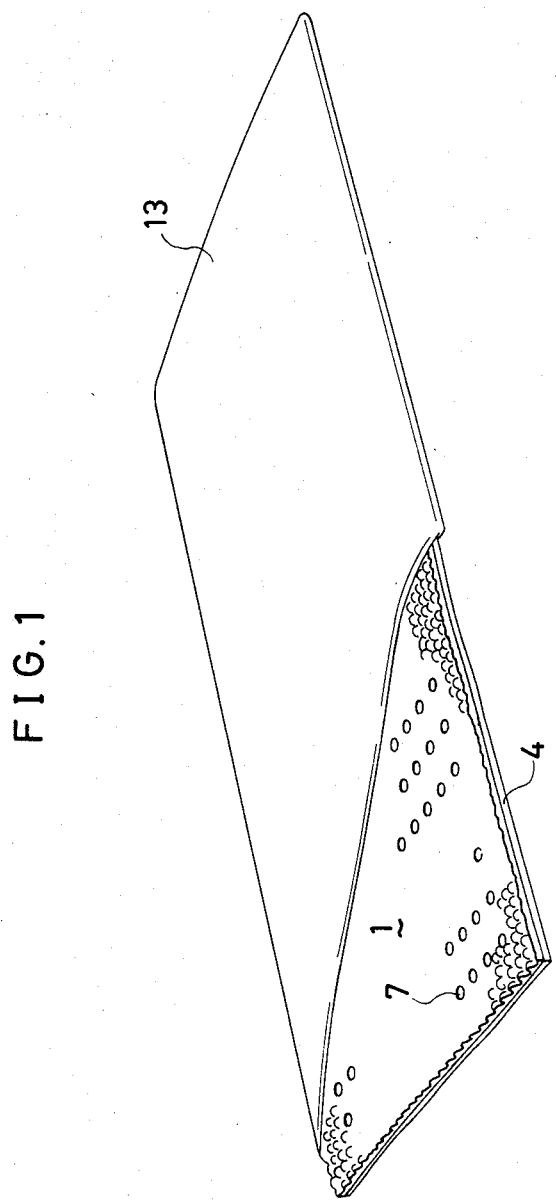

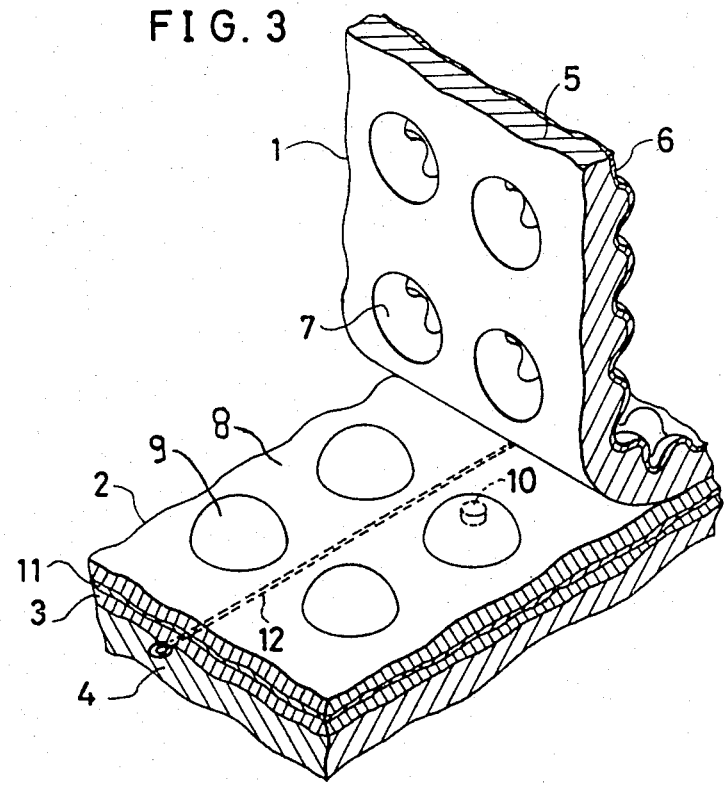

SLEEPING MATTRESS

BACKGROUND OF THE INVENTION

1. Field of the Invention

The present invention is concerned with a sleeping mattress, particularly a magnetic sleeping mattress having a magnetic curing effect.

2. Description of the Prior Art

Sleep is indispensable to the human being. It is necessary for deep sleep to assume the right posture during lying on a mattress, that is, to stretch the back bone so that the organs of the human body are relaxed.

Many illnesses have been caused by curved back bones. In this regard, existing mattresses do not deal with the necessity of keeping the back bone balanced and smoothly circulating the blood for removing stiffness in the shoulders or tiredness. Therefore, an ideal sleeping posture could not be obtained.

SUMMARY OF THE INVENTION

A main object of the invention is to provide a sleeping mattress by which the back bone is kept straight during sleeping and the blood is smoothly circulated due to its magnetic effect to remove stiffness in the shoulders or fatique.

Another object of the invention is to provide a sleeping mattress which is excellent in air permeability and thereby cool in the summer and warm in the winter.

A further object of the invention is to provide a sleeping mattress having a magnetic curing effect.

A still further object of the invention is to provide a sleeping mattress which is moderate in hardness balancing as a whole, and holds its shape.

These objects and advantages are achieved by a sleeping mattress comprising, in order:
- a first layer made of cushion material having a plurality of holes therein, formed with an undulated outer surface;
- a second layer having semicicular projections provided with magnets, said semicircular projections being mated with said holes;
- a third layer stuffed with fibers and reinforcing materials; and
- a fourth layer comprising cushion material.

Other objects and advantages to be brought about by the invention will be apparent from description of the invention with reference to the attached drawings.

BRIEF DESCRIPTION OF THE DRAWINGS

FIG. 1 is a perspective view of the invention,

FIG. 2 is a vertical cross sectional view showing an inner structure of the sme, FIG. 3 is a view showing an example of arranging magnets and reinforcing materials.

DETAILED DESCRIPTION OF THE INVENTION

Figure 4:
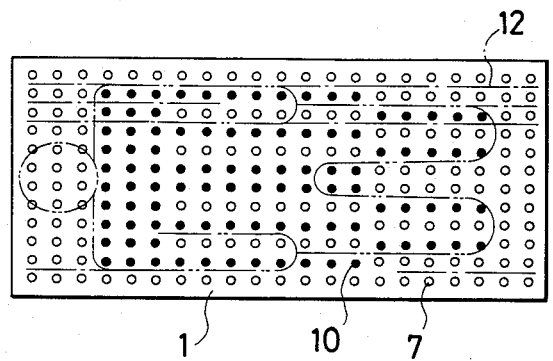
FIG. 4 is a view showing an example of arranging magnets and steel materials.

A mattress according to the invention comprises a structure of four layers in which a first layer 1 is a wave, or undulated, layer, a second layer 2 is a magnetic layer including magnets, a third layer 3 is a compression palm lock layer, and a fourth layer 4 is a cushion layer.

The first layer 1 is for balancing the body weight in uniform dispersion and giving a soft massaging effect to the body. This layer comprises a cushion material of about 2 cm in thickness. Preferably a urethane form 5, is formed thereon with a thin outer cover 6 and is perforated with holes regularly lengthwise and crosswise. The urethane form 5 is provided with a plurality of wave-like undulations regularly lengthwise and crosswise, and the thin outer cover 6 is impregnated with resin liquid such as urethane. Concerning the number of the holes, about 21×12 are required for the size of the product being 1950 (length)mm×930 (width)mm, and about 21-20 are required for 1950×1300. Permanent magnets as later mentioned are exposed at the holes 7.

The second layer 2 is for naturally straightening the spine while giving a magnetic effect to the body. In this layer, the thin sheet 8 made of urethane foam is arranged thereon with semi-circle projections 9 in parallel, and the desired projections 9 are laid with ferrite permanent magnets 10. The second layer 2 is, as later mentioned, made integral with a third layer 3 via hard grains 11 of urethane resin and adhesives so that it holds the shape of the mattress.

Figures 5A, 5B:
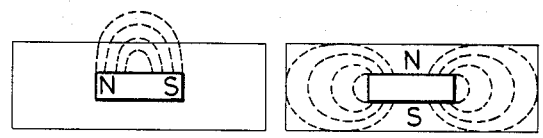
FIG. 5A is a view showing magnetic line of force of a conventional magnet.
FIG. 5B is a view showing the magnetic lines of force of the invention.

A permanent magnet 10, having poles at one side (magnetism on one side) is used. Thereby, the magnetic lines of force reach far (see FIG. 5B) in comparison with conventional magnets (see FIG. 5A). Thus, the magnetic effect serves at deeper parts of the human body so that the blood runs actively and stiffness is removed from the body. In order to provide the maximum curing effect, it is preferable to deposit the permanent magnets 10 having 850 gauss at parts nearest to the human body, that is, at the projections 9. However, the magnets 10 are covered with thin sponge or cloth for preventing any unpleasent feeling caused by directly touching the skin. The magnets 10 are not necessarily all arranged within the projections 9, but may be gathered at the parts corresponding to the shoulders, back, waist or legs. FIG. 4 illustrates an example of such an arrangement with black marks.

A third layer 3 is for maintaining moderate hardness over the entire mattress in order to prevent the spine from curving due to unnatural sinking of the body. This layer comprises compressed fibers such as palm or the like, and is arranged with reinforcing material, for example, steel wires 12 of around 3 mm in diameter thereover with appropriate space for providing greater rigidity. For a three-fold type, the steel lines 12 are arranged in division lengthwise. For a non-folding type, the steel wire 12 may be divided appropriately. The third layer 3 integrally holds grains 11 of hard urethane resin and binding agent between the second layer 2 and itself and has many concave and convex regions, and the concave regions fit within the projections 9, which concave regions have a shape to interlock with projections 9. In such a manner, the semi-circular shape of the projections 9 is firmly supported and prevented from depression.

The fourth layer 4 is for supporting the mattress as a whole effecting moderate cushioning and softening vibration of the body. This layer is in general made of urethane foam.

The mattress composed of the four layers may be of a three-fold or a non-folding type. In use, the mattress is protected with a cover 13.

Effects brought about by the four layered structure are as follows:

(1) By wave-like projections of the first layer and projections 9 of the second layer, the body weight is dispersed in balance while a soft massaging effect is obtained. Through the projections and the compressed palm layer of the third layer, evaporation of the moisture from sweat and other sources is accelerated so that an ideal feeling of warmth in the winter and coolness in the summer is effected.

(2) The magnets arranged in the second layer act on the human body as follows:
  A. Magnetising the human body
  B. Generating new electricity with the body
  C. Generating electric current in the blood
  D. Increasing ion concentration in the blood
  E. Changing the action of the autonomic nervous system
  F. Smoothing circulation of the blood
  G. Improving stiffness or ill conditions (3) Grains of hard urethane resin between the second and third layers, and the third layer including the reinforcing material give moderate rigidity over the mattress, and the back bone is kept in straight during lying on the mattress.

(4) The lowest urethane foam layer gives a comfortable cushion feeling.

What is claimed is:

1. A sleeping mattress comprising, in order:
   a first layer made of cushion material, having a plurality of holes therein, formed with an undulated outer surface;
   a second layer having semicircular projections provided with magnets, said semicircular projections being mated with said holes;
   a third layer stuffed with fibers and reinforcing materials; and
   a fourth layer comprising cushion material.

2. A sleeping mattress as claimed in claim 1, wherein each of said permanent magnets has both poles on one side thereof.

3. A sleeping mattress as claimed in claim 1, wherein said permanent magnets are disposed at points corresponding to the shoulders, arms, spine, waist and legs of a human being lying upon said mattress.

4. A sleeping mattress as claimed in claim 1, wherein each of the permanent magnets is 850 gauss.

5. A sleeping mattress as claimed in claim 1, wherein the permanent magnets are positioned on said projections.

6. A sleeping mattress as claimed in claim 1, wherein the reinforcing materials are steel wires.

7. A sleeping mattress as claimed in claim 1, wherein the semi-circular shapes of the projections holding the magnets therein are supported by means of convex regions formed in the third layer.

* * * * *